United States Patent
Moore et al.

(10) Patent No.: US 9,663,389 B1
(45) Date of Patent: May 30, 2017

(54) USE OF MGO DOPED WITH A DIVALENT OR TRIVALENT METAL CATION FOR REMOVING ARSENIC FROM WATER

(71) Applicant: Sandia Corporation, Albuquerque, NM (US)

(72) Inventors: Robert C. Moore, Edgewood, NM (US); Kathleen Caroline Larese, Rio Rancho, NM (US); Ranko Panayotov Bontchev, Albuquerque, NM (US)

(73) Assignee: Sandia Corporation, Albuquerque, NM (US)

( * ) Notice: Subject to any disclaimer, the term of this patent is extended or adjusted under 35 U.S.C. 154(b) by 507 days.

(21) Appl. No.: 13/964,424

(22) Filed: Aug. 12, 2013

Related U.S. Application Data

(62) Division of application No. 12/336,953, filed on Dec. 17, 2008, now Pat. No. 8,507,004.

(51) Int. Cl.
  *B01J 20/04* (2006.01)
  *C02F 1/62* (2006.01)

(52) U.S. Cl.
  CPC ..................... *C02F 1/62* (2013.01)

(58) Field of Classification Search
  None
  See application file for complete search history.

(56) References Cited

U.S. PATENT DOCUMENTS

| | | |
|---|---|---|
| 4,935,146 A | 6/1990 | O'Neill et al. |
| 6,416,252 B1 | 7/2002 | Moore |
| 6,592,294 B1 | 7/2003 | Moore |
| 6,802,980 B1 * | 10/2004 | Khandaker et al. .......... 210/724 |
| 6,821,434 B1 | 11/2004 | Moore et al. |
| 6,824,690 B1 | 11/2004 | Zhao et al. |
| 6,830,695 B1 | 12/2004 | Brady et al. |
| 6,843,617 B2 | 1/2005 | Chowdhury et al. |
| 7,074,336 B1 | 7/2006 | Teter et al. |
| 7,122,502 B1 | 10/2006 | Teter et al. |
| 7,247,242 B1 * | 7/2007 | Moore et al. .................. 210/662 |
| 2002/0113023 A1 | 8/2002 | Krulik et al. |

FOREIGN PATENT DOCUMENTS

| | | |
|---|---|---|
| JP | 10338818 A | * 12/1998 |
| JP | 2000070927 A | * 3/2000 |

* cited by examiner

*Primary Examiner* — Robert A Wax
*Assistant Examiner* — William Craigo
(74) *Attorney, Agent, or Firm* — Daniel J. Jenkins

(57) ABSTRACT

Systems and methods for use of magnesium hydroxide, either directly or through one or more precursors, doped with a divalent or trivalent metal cation, for removing arsenic from drinking water, including water distribution systems. In one embodiment, magnesium hydroxide, $Mg(OH)_2$ (a strong adsorbent for arsenic) doped with a divalent or trivalent metal cation is used to adsorb arsenic. The complex consisting of arsenic adsorbed on $Mg(OH)_2$ doped with a divalent or trivalent metal cation is subsequently removed from the water by conventional means, including filtration, settling, skimming, vortexing, centrifugation, magnetic separation, or other well-known separation systems. In another embodiment, magnesium oxide, MgO, is employed, which reacts with water to form $Mg(OH)_2$. The resulting $Mg(OH)_2$ doped with a divalent or trivalent metal cation, then adsorbs arsenic, as set forth above. The method can also be used to treat human or animal poisoning with arsenic.

3 Claims, 1 Drawing Sheet

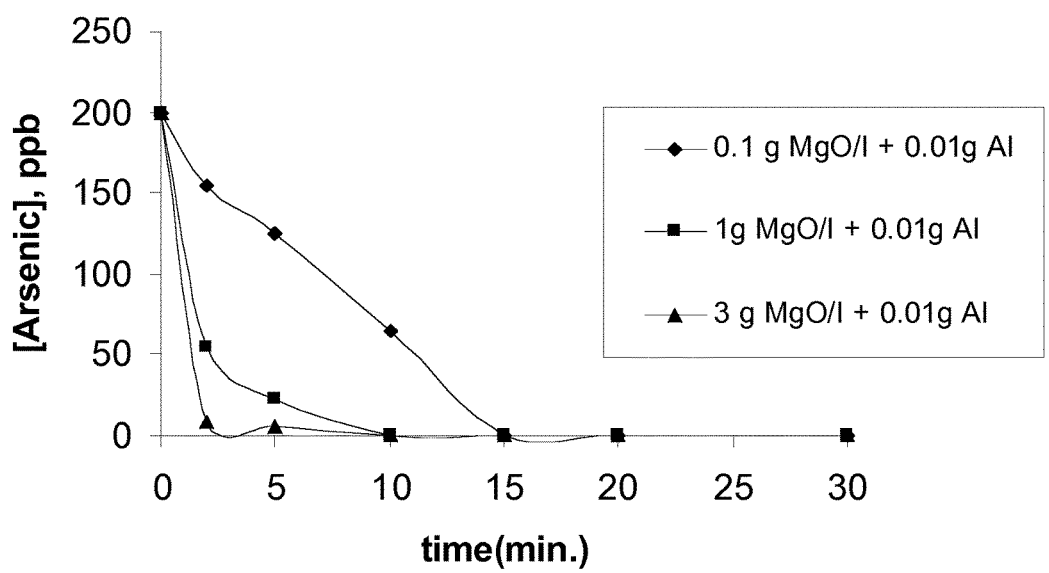

US 9,663,389 B1

USE OF MGO DOPED WITH A DIVALENT OR TRIVALENT METAL CATION FOR REMOVING ARSENIC FROM WATER

CROSS-REFERENCE TO RELATED APPLICATIONS

This application is a divisional application of U.S. Ser. No. 12/336,953, Use of MgO Doped with a Divalent or Trivalent Metal Cation for Removing Arsenic from Water, by Robert C. Moore et al., filed Dec. 17, 2008, which is incorporated herein by reference.

FEDERALLY SPONSORED RESEARCH

The United States Government has rights in this invention pursuant to Department of Energy Contract No. DE-AC04-94AL85000 with Sandia Corporation.

BACKGROUND OF THE INVENTION

The present invention relates to systems for removal of arsenic from water, and more specifically from municipal or rural water systems, utilizing magnesium hydroxide doped with a divalent or trivalent metal cation as an adsorbent for arsenic.

The presence of arsenic in drinking water is a significant health concern. Chronic exposure to arsenic has been linked to cancer. The current drinking water regulations by the United States Environmental Protection Agency set the maximum contamination limit (MCL) of arsenic at 10 parts per billion (ppb). By reducing arsenic exposure, the risk of cancer is reduced. The presence of arsenic in drinking water in excess of the MCL affects many municipal water systems across the United States, particularly those drawing from ground water sources. Effective and efficient removal of arsenic from drinking water is of primary concern. Ground water obtained from areas with geologic evidence of volcanic activity, both high arsenic levels and high mineral content, including carbonates, are generally problematic. Current technologies are less effective for influent water that contains minerals, including carbonates. There have been a number of systems used to remove arsenic and other heavy metals from water, including reverse osmosis, column purification, and hydroxide precipitation. Many of these processes provide acceptable results only within narrow and restrictive parameters and are highly dependent on site-specific water chemistry. Due to this inefficiency, many of these processes are costly and comparatively inefficient.

None of the prior systems meet the requirements of efficient removal of arsenic utilizing commonly and inexpensively available reagents with a minimum of mechanical processing and steps. Thus there is a need for an inexpensive and simple process that specifically removes arsenic from drinking water, in the presence of other minerals.

In addition to the treatment of water to remove arsenic, quantitative measurement of arsenic concentration in water at 1-50 ppb levels requires expensive and complex equipment that is not feasible for small and medium-sized municipal water treatment facilities. Thus, there is a need for a system for concentrating arsenic from less than 50 ppb to higher, more easily detectable concentrations in water (preferably by a factor of at least 10 to 30 times). Detection of arsenic at a 100 ppb level and above allows for less expensive equipment and less complex techniques to be used for arsenic quantification.

SUMMARY OF THE INVENTION

The invention provides systems and methods for use of magnesium hydroxide, either directly or through one or more precursors, doped with a divalent or trivalent metal cation, for removing arsenic from drinking water, including water distribution systems. In one embodiment, magnesium hydroxide, $Mg(OH)_2$ (a strong adsorbent for arsenic) doped with a divalent or trivalent metal cation is used to adsorb arsenic. The complex consisting of arsenic adsorbed on $Mg(OH)_2$ doped with a divalent or trivalent metal cation is subsequently removed from the water by conventional means, including filtration, settling, skimming, vortexing, centrifugation, magnetic separation, or other well-known separation systems. In another embodiment, magnesium oxide, MgO, is employed, which reacts with water to form $Mg(OH)_2$. The resulting $Mg(OH)_2$ doped with a divalent or trivalent metal cation, then adsorbs arsenic, as set forth above. The method can also be used to treat human or animal poisoning with arsenic.

BRIEF DESCRIPTION OF THE DRAWINGS

The accompanying drawings, which are incorporated in and form part of the specification, illustrate various examples of the present invention and, together with the detailed description, serve to explain the principles of the invention.

FIG. 1 shows a graph of arsenic concentration in ppb versus time in minutes, illustrating the kinetics of arsenic sorption by MgO doped with a divalent or trivalent metal cation.

DETAILED DESCRIPTION OF THE INVENTION

Magnesium oxide is currently used in water treatment operations for pH adjustment and water softening. In this work, it was unexpectedly discovered that arsenic dissolved in water can be more strongly sorbed using MgO or $Mg(OH)_2$ when doped with a divalent or trivalent metal cation, specifically zinc or aluminum. Experiments were performed by adding various sorbents to a liter of distilled water containing arsenic(V) and shaking for 1 hour. The sorbents tested were selected from the group consisting of: 0.2 g of MgO, 0.2 g $Mg(OH)_2$, 0.2 g MgO doped with a small amount of a zinc salt, and 0.2 g MgO doped with a small amount of an aluminum salt. The arsenic remaining in solution was measured by ICP-MS. The results are given in Table 1. As seen in the table, the order of arsenic sorption was: $Mg(OH)_2 < MgO < MgO+Zn < MgO+Al$.

Magnesium oxide, fired at low temperature to remain reactive in water and convert to magnesium hydroxide, can be used with an added divalent or trivalent metal cation, $Zn^{2+}$ or $Al^{3+}$, in a process to remove arsenic from water. The magnesium oxide/magnesium hydroxide solids with sorbed arsenic can be removed by conventional treatment processes such as filtration, flocculation and settling or precipitation or other means. After treatment, if desirable, the pH of the water can be adjusted for drinking water using conventional methods such as chemical treatment or sparging with carbon dioxide in air. The addition of a divalent or trivalent metal cation, specifically $Zn^{2+}$ and $Al^{3+}$ greatly enhances the sorption of arsenic.

The added divalent or trivalent metal cation, e.g., $Zn^{2+}$ or $Al^{3+}$, can be supplied from the following examples of metal cation salts: zinc sulfate, hydrous zinc sulfate, zinc chloride, zinc nitrate, and anhydrous zinc nitrate; and aluminum chloride, aluminum nitrate, aluminum phosphate, aluminum sulfate, etc.

The length of time required for adsorption of the desired quantity of arsenic is dependent on a variety of factors, including pH and temperature of the water, quantity of arsenic present in the water and quantity of carbonates, including bicarbonates, present in the water. For most applications, the doped $Mg(OH)_2$ is maintained in the water for less than one hour, and preferably less than about thirty minutes. In general, rapid removal of the doped $Mg(OH)_2$ is desired, to prevent conversion of $Mg(OH)_2$ to $MgCO_3$ by native carbonates, and thus systems such as settling are not as effective unless carbonate concentrations are very low, or unless flocculating agents to aid in settling are employed. Separation can be done by a filtration assembly, a vortex separator, a centrifugal separator, a combination of the foregoing, or any means for removal of insoluble particles of doped $Mg(OH)_2$ with adsorbed arsenic.

In removal systems employing settling, such as with $Mg(OH)_2$ or $Ca(OH)_2$, or a precursor thereto, a flocculating agent may be employed to aid in settling. Such agents increase the speed of settling, thereby permitting removal of, for example, $Mg(OH)_2$ prior to conversion to $MgCO_3$ due to the presence of $CaCO_3$ in the water. Various clays and polymers, known to those skilled in the art, may be employed to aid in settling of either $Mg(OH)_2$ or $Ca(OH)_2$ from water.

If the water to be treated contains a large amount of carbonate, then more MgO or $Mg(OH)_2$ can be used to remove the arsenic. The presence of carbonate does not stop the adsorption of arsenic onto the $Mg(OH)_2$, but reduces the efficiency of the process of adsorption of arsenic, in part by conversion of $Mg(OH)_2$ to $MgCO_3$, and also by concomitant release of adsorbed arsenic.

In general, the adsorption of arsenic onto $Mg(OH)_2$ is a rapid reaction, and generally less than one minute of contact time is required. A kinetic study was performed and the results are given in FIG. 1. The FIGURE shows very rapid sorption of arsenic with MgO doped with Al.

However, the rate of arsenic adsorption, as well as the rate for conversion of $Mg(OH)_2$ to $MgCO_3$, is temperature and pH dependent. At higher pH levels, the rate of formation of $MgCO_3$ is generally relatively decreased more than the rate of arsenic adsorption onto $Mg(OH)_2$, such that pH adjustment may be employed to insure arsenic adsorption without formation of magnesium carbonate overwhelming the arsenic adsorption.

MgO will convert to $Mg(OH)_2$ upon adding to water. The reaction is pH and temperature dependent, and strongly depends on the crystallinity of the MgO used. MgO will hydrate to $Mg(OH)_2$ rapidly, within a few minutes, in water if the MgO was originally prepared by heating to only a low temperature. MgO prepared by heating to a low temperature is termed "reactive MgO". If the MgO was prepared by heating to a high temperature (400° C.-1500° C.), a more crystalline material is formed. The highly crystalline form of MgO can take days, weeks, or even months to convert to $Mg(OH)_2$. In the present invention, the use of "reactive MgO" is preferred because of the more rapid conversion to $Mg(OH)_2$. However, highly crystalline MgO can be employed, particularly if it is first pretreated to decrease its crystallinity (which involves soaking in water that is heated to high temperature under high pressure). Either form of MgO cost roughly the same.

$Mg(OH)_2$ is essentially insoluble in water over normal pH ranges and temperatures encountered in water distribution systems. $Mg(OH)_2$ is available, and may be employed in this invention, in any of a variety of suspensions, slurries, powders or particulates. In one embodiment, a magnesium hydroxide suspension is employed, containing at least 98% $Mg(OH)_2$ with a median particle size less than 3 microns, and preferably 0.5-1.0 microns, in a suspension of water. In another embodiment, $Mg(OH)_2$ powder may be employed, of a powder size sufficiently small to essentially all pass through a 325 mesh screen, and with a surface area from about 7 to about 13 $m^2/gm$. In another embodiment, the MgO or $Mg(OH)_2$ powder has a median particle size less than 3 microns.

A variety of techniques can be used to remove the $Mg(OH)_2$ after arsenic has adsorbed to its surface. Such a system can be either a batch or continuous process. In a batch treatment system, a sufficient amount of MgO or $Mg(OH)_2$ is added to a container of water contaminated with arsenic. The $Mg(OH)_2$ is stirred to keep it in suspension for a sufficient period of time to adsorb the desired amount of arsenic.

Since $Mg(OH)_2$ has a $K_d$, or sorption coefficient defined as ((mole arsenic adsorbed/mole $Mg(OH)_2$)/mole/kg arsenic in water), equal to $1.1 \times 10^6$, a small amount of MgO or $Mg(OH)_2$ will treat a very large amount of arsenic contaminated water. Adding more than the minimum amount will serve to increase the rate at which the arsenic concentration decreases over time. The concentration of doped MgO or $Mg(OH)_2$ added to water can be between 0.1 g/L and 0.5 g/L. The concentration of the added divalent or trivalent metal cation (i.e., $Zn^{2+}$ or $Al^{3+}$) can be between 0.001 g/L and 0.1 g/L; and preferably about 0.01 g/L.

Since $Mg(OH)_2$ is heavier than water, particles of doped $Mg(OH)_2$ with adsorbed arsenic will eventually settle out as a sludge on the bottom of a container of quiescent water. The settled particles can subsequently can be removed by draining them through a open valve in a bottom of the container, or by vacuuming out the sludge with a tube or hose, or by pouring out the water from the top without disturbing and re-suspending the settled particles. Flocculants can be added to enhance the settling action. Alternatively, the mixture can be kept in suspension, and then poured through a filter, whereby $Mg(OH)_2$ with adsorbed arsenic remains on the filter media and purified water passes through.

Alternatively, an dissolved air floatation apparatus can be used, whereby air (or other buoyant gas) is bubbled up from the bottom of a tank, whereby particles of $Mg(OH)_2$ with adsorbed arsenic attach to the gas bubbles and float to the top, where they can be skimmed off, leaving purified water behind.

Optionally, after separation and removal of $Mg(OH)_2$ with adsorbed arsenic from the water, the pH of the purified water can be adjusted appropriately, as needed.

Alternatively, the MgO or $Mg(OH)_2$ sorbent material can be coated onto a carrier or substrate particle, such as sand or glass microspheres. If the carrier particle is magnetic (such as containing iron), then magnetic separation can be used to efficiently and rapidly separate these particles of arsenic adsorbed on the $Mg(OH)_2$. If the carrier particle, including $Mg(OH)_2$ coating, is denser than water, then gravity can be used to settle and separate the particles. The larger the density difference with water, the more efficient the use of centrifugal and vortex separation processes. Alternatively, the carrier particle can be a lighter-than-water material (such as plastic or polystyrene microspheres), which would float to the surface where they can be easily skimmed off.

The separator can be a vortex separator, centrifugal separator or filter depending on the size of $MgO/Mg(OH)_2$ particles injected into the water stream to remove the arsenic. Additionally, a holding tank may optionally be included to provide the necessary contact time for the $Mg(OH)_2$ to remove the arsenic. A holding tank may not be needed for certain systems. A recycle stream can be substituted for the holding tank.

Any of the systems for removing arsenic from water that are taught in U.S. Pat. No. 6,821,434, "System for Removal of Arsenic From Water", to Moore et al., (which is herein incorporated by reference) can be used with the present method of removing arsenic from water by using MgO or $Mg(OH)_2$ doped with a divalent or trivalent metal cation, according to the present invention.

The divalent or trivalent metal cation (e.g., Zn or Al), can be added in the form of a metal salt to the arsenic-contaminated water independently from adding the magnesium hydroxide to the water.

Alternatively, the divalent or trivalent metal cation can be combined with particles or powders of magnesium hydroxide before being added to water. For example, the magnesium hydroxide particles can be coated with a small amount of zinc or aluminum. Or, magnesium hydroxide particles can be pre-mixed with a small amount of zinc or aluminum. In this way, the magnesium hydroxide particles are pre-doped with the divalent or trivalent metal cation.

In addition to water treatment, the use of $Mg(OH)_2$ as a treatment for arsenic poisoning has been reported. Because of its stronger sorption capacity, the addition of a small amount of a divalent or trivalent ion, specifically Zn or Al, is much more effective. Magnesium oxide, fired at low temperature to remain reactive in water and convert to magnesium hydroxide, can be used with an added divalent or trivalent metal cation, $Zn^{2+}$ or $Al^{3+}$, as a treatment for arsenic poisoning. In the stomach MgO would rapidly convert to $Mg(OH)_2$ and form a layered structure. $Mg(OH)_2$ is a safe compound for ingestion and is commonly used as an antacid and laxative. The magnesium compound with sorbed arsenic can be expelled from the stomach after arsenic sorption is complete by physical or chemical means to cause vomiting of because of the laxative effect of $Mg(OH)_2$ it can pass through the digestive system. Treatment with MgO or $Mg(OH)_2$ doped with the cation can be used with other treatment options to enhance the treatment process.

Table 1. Sorption of arsenic from water using magnesium compounds and magnesium compounds doped with zinc and aluminum. 0.2 g of MgO or $Mg(OH)_2$ in 1 L of arsenic solution. Zinc and aluminum were added as $AlCl_3$ and $ZnCl_2$.

| Additive | Dilution factor for ICP-MS analysis | [As] remaining in solution after treatment, (ppb) | % arsenic sorbed |
|---|---|---|---|
| 100 ppm As(V) + 0.2 g $Mg(OH)_2$ | 100 | 1040.1 | 1 |
| 10 ppm As(V) + 0.2 g $Mg(OH)_2$ | 10 | 1007.2 | 11 |
| 1 ppm As(V) + 0.2 g $Mg(OH)_2$ | 1 | 826.7 | 34 |
| 100 ppm As(V) + 0.2 g MgO | 100 | 928.6 | 20 |
| 100 ppm As(V) + 0.2 g MgO | 10 | 388.8 | 67 |
| 100 ppm As(V) + 0.2 g MgO | 1 | 120.9 | 90 |
| 100 ppm As(V) + 0.2 g $Mg(OH)_2$ + 0.01 g $Al^{3+}$ | 100 | 991.7 | 7 |
| 10 ppm As(V) + 0.2 g $Mg(OH)_2$ + 0.01g $Al^{3+}$ | 10 | 938.1 | 15 |
| 1 ppm As(V) + 0.2 g $Mg(OH)_2$ + 0.01g $Al^{3+}$ | 1 | 627.3 | 50 |
| 100 ppm As(V) + 0.2 g MgO + 0.01 g $Al^{3+}$ | 100 | 831.1 | 29 |
| 10 ppm As(V) + 0.2 g MgO + 0.01 g $Al^{3+}$ | 10 | 179.6 | 82 |
| 1 ppm As(V) + 0.2 g MgO + 0.01 g $Al^{3+}$ | 1 | 5.9 | 100 |
| 100 ppm As(V) + 0.2 g $Mg(OH)_2$ + 0.01 g $Zn^{2+}$ | 100 | 984.4 | 14 |
| 10 ppm As(V) + 0.2 g $Mg(OH)_2$ + 0.01 g $Zn^{2+}$ | 10 | 867.1 | 16 |

The particular examples discussed above are cited to illustrate particular embodiments of the invention. Other applications and embodiments of the apparatus and method of the present invention will become evident to those skilled in the art. It is to be understood that the invention is not limited in its application to the details of construction, materials used, and the arrangements of components set forth in the following description or illustrated in the drawings.

The scope of the invention is defined by the claims appended hereto.

What is claimed is:

1. A composition of matter, comprising:
    particles of MgO or $Mg(OH)_2$ having a zinc coating;
    wherein the median particle size is less than 3 microns; and
    wherein the zinc coating is present as any one of zinc sulfate, hydrous zinc sulfate, zinc chloride, zinc nitrate, and anhydrous zinc nitrate.

2. The composition of claim 1, wherein the zinc coating is 5% of the mass of the MgO or $Mg(OH)_2$ coated particles.

3. The composition of claim 1, wherein the particles have a diameter of between 0.5 and 1.0 microns.

* * * * *